United States Patent [19]

Runner

[11] Patent Number: 5,243,298
[45] Date of Patent: Sep. 7, 1993

[54] CORROSION MONITOR BY CREATING A GALVANIC CIRCUIT BETWEEN AN ANODE WIRE AND A TEST STRUCTURE

[75] Inventor: Jack A. Runner, San Diego, Calif.

[73] Assignee: Teledyne Ryan Aeronautical, Division of Teledyne Industries, Inc., San Diego, Calif.

[21] Appl. No.: 787,689

[22] Filed: Nov. 4, 1991

[51] Int. Cl.⁵ .................... G01R 27/08; G01N 17/00
[52] U.S. Cl. ............................ 324/700; 324/71.1; 324/71.2; 324/699; 204/153.11; 204/404; 73/86
[58] Field of Search ............. 324/691, 699, 700, 557, 324/71.2, 71.1; 73/86; 204/153.11, 404

[56] References Cited

U.S. PATENT DOCUMENTS

| | | |
|---|---|---|
| 3,108,242 | 10/1963 | Scott . |
| 3,549,993 | 12/1970 | Marsh et al. ............. 324/71.1 |
| 4,380,763 | 4/1983 | Peart et al. .............. 324/700 |
| 4,703,255 | 10/1987 | Strommen ............. 204/153.11 |
| 4,780,664 | 10/1988 | Ansuini et al. ............ 324/700 |
| 4,806,849 | 2/1989 | Kihira et al. . |
| 4,839,580 | 6/1989 | Moore et al. . |
| 5,036,287 | 7/1991 | Serwatzky ............... 324/700 |

OTHER PUBLICATIONS

Edmund C. Potter, *Electrochemistry Principles & Applications*, 1961, pp. 262 and 263.

Primary Examiner—Gerard R. Strecker
Assistant Examiner—Diep Do
Attorney, Agent, or Firm—Brown, Martin, Haller & McClain

[57] ABSTRACT

A corrosion monitoring system having one or more anode elements made of a suitable anodic material that corrodes preferentially with respect to the structure being protected. The resistance of each anode wire is continuously or periodically monitored. The presence of moisture between an anode and the structure being monitored creates a current path and causes galvanic corrosion. The anode wire will begin to corrode, but the structural members will remain uncorroded until the anode has been completely consumed. The monitoring system uses the rate of change in anode resistance to extrapolate a prediction of the time remaining before the structure being protected begins to corrode.

10 Claims, 1 Drawing Sheet

CORROSION MONITOR BY CREATING A GALVANIC CIRCUIT BETWEEN AN ANODE WIRE AND A TEST STRUCTURE

BACKGROUND OF THE INVENTION

My invention relates generally to corrosion monitoring and, more specifically, to a corrosion monitoring apparatus for providing an estimate of the remaining service life of a structure before the onset of galvanic corrosion.

Metallic structural members of aircraft, ships and other equipment are subject to galvanic corrosion in the presence of moisture. Galvanic corrosion occurs as a result of current generated by the electrochemical reaction between dissimilar metals in the presence of an electrolyte. Furthermore, certain metal alloys are susceptible to corrosion because they comprise two or more metals.

Inspection for corrosion damage is difficult because corrosion frequently occurs in inaccessible areas of the structure. Aircraft wings often cannot be nondestructively inspected because the skin is bonded to the interior support structure. Furthermore, visual inspection techniques cannot precisely estimate the remaining service life of a structure known to have corrosion damage.

Dissimilar metals in aircraft and other equipment are typically insulated from contact with one another by a moisture barrier. In an aircraft wing, for example, the skin is insulated from the interior structure. During manufacturing, the interior structure is heat-treated to remove moisture prior to being insulated and sealed by bonding the skin to it. However, imperfections or punctures in the skin or insulation can allow moisture to provide a current path between the metals. This current causes corrosion of the metals over a period of time.

Practitioners in the art have developed systems for monitoring the progress of corrosion. U.S. Pat. No. 4,380,763 issued to Peart et al. discloses a system having galvanic sensors that are instead into a corrosive environment, such as in the inaccessible recesses of an aircraft frame. Each sensor of Peart et al. comprises anode and cathode elements made of dissimilar metals. The sensor generates a detectable current when exposed to moisture. Peart et al. disclose an integrating means for measuring the cumulative current flow, which is representative of the extent of corrosion. Peart et al. disclose that the sensor metals must be identical to the metals used in the structure to obtain an accurate indication of corrosion. If the metals are not identical or the sensor is not exposed to precisely the same corrosive environment as the structure, the measurements will be inaccurate. Furthermore, the measuring device of Peart et al. must store the value representing cumulative current flow over the service life of the structure being monitored. Peart et al. use a nonvolatile memory and complex support circuitry for integrating and storing the cumulative current flow. The system is completely useless in the event that this value is lost.

U.S. Pat. No. 4,839,580 issued to Moore et al. discloses a correction monitoring sensor that utilizes the principle that the resistance of the sensor element acting as the galvanic anode increases as the anode element itself corrodes. The sensors of Moore et al. comprise a stainless steel frame having sensor portions and reference portions, each plated with a layer of metal. Corrosion monitoring systems based upon anode resistance are simpler, more reliable, and more accurate than those based upon cumulative current flow. Furthermore, sensor elements used in these systems need not be constructed of the same metals used in the structure being monitored because the rate of change in sensor element resistance is proportional to the corrosion rate of the structure.

The sensitivity of anode resistance sensors to incremental resistance change is inversely proportional to anode thickness. While a very thin anode element provides a large change in resistance in response to a small degree of corrosion, the anode must be thick enough to eliminate the need for frequent replacement. The corrosion monitoring system becomes useless if the anode element corrodes through, resulting in an open circuit. The sensor of Moore et al. is designed for continuously monitoring a corrosive environment by measuring the resistance change of a sensor pre-plated with a corrodable metal or, conversely, for monitoring electrolytic plating processes by measuring the resistance change of a sensor as the plating metal builds up of the sensor. The sensor of Moore et al. is designed to be reusable by removing it from the corrosive environment and replating it. The need to achieve a long useful sensor life inherently sacrifices sensor sensitivity.

It is well-known that metallic structural members can be protected from galvanic corrosion by providing the structural members with an anodic material that corrodes preferentially with respect to the structure, thereby sacrificially corroding the anodic material and preserving the structural members. Practitioners in the art have protected metal structures using this principle by applying a primer coating to the portion of the metal exposed to moisture. The primer applied to aluminum structures typically contains zinc, which corrodes preferentially with respect to aluminum. Similarly, ships and heavy equipment in which additional weight is not a critical design consideration have been protected by attaching plates of preferentially corroding anodic material to the hull or other structure. The structure will begin to corrode when the anodic material is completely consumed by the electrochemical reaction.

In aircraft, however, weight considerations prohibit providing enough anodic material to completely guard against corrosion of the structural members over the service life of the aircraft. Therefore, as discussed above, practitioners in the art have guarded against corrosion by sealing areas of the aircraft structure that would be particularly susceptible to corrosion. Moisture entering these sealed, uninspectable areas may cause undetected corrosion, which if allowed to progress, could cause catastrophic structural failure.

Simply detecting a moisture intrusion into these sealed areas with a galvanic sensor provides no warning period; corrosion may begin as soon as moisture has entered. Furthermore, anodic resistance sensors such as that of Moore et al. are not well-suited for use in aircraft, which require economical monitoring of a large area with a minimum contribution to weight. A reusable sensor is unnecessary in monitoring sealed, inaccesible areas of an aircraft because the area must be opened once corrosion has been detected.

It would be desirable to provide an accurate indication of the corrosive effect on the structure of any such moisture intrusion. It would further be desirable to provide an indication of the time remaining before the onset of structural corrosion to aid in decisions concerning continued use of the aircraft or its return for depot-level maintenance. Such an aid would provide a valuable maintenance scheduling tool by reducing guesswork, resulting in greater efficiency.

There is a strongly felt need in the art for a system that provides an accurate indication of the remaining service life of a structure as well as a buffer of "temporary protection," during which period decisions regarding the scheduling of aircraft maintenance can be made. These problems and deficiencies are clearly felt in the art and are solved by my invention in the manner described below.

SUMMARY OF THE INVENTION

My invention comprises one or more anode elements made of a suitable anodic material that corrodes preferentially with respect to the structure being protected. Practitioners in the art can readily determine a suitable preferentially corroding material with respect to the composition of any metallic structure. For example, because zinc is known to corrode preferentially with respect to aluminum, zinc anode elements may be used to monitor the corrosion of aluminum structures. Incremental changes in anode element resistance are monitored using conventional measuring means.

The anode elements should be thin wires to provide good sensitivity to small changes in resistance while maximizing coverage of the area of the aircraft to be protected with minimal additional weight. The anode wires are located in inaccessible areas of the structure likely to experience moisture intrusions, such as the wing interior or the lavatory area of the fuselage in commercial airliners. In an aircraft wing, for example, a skin is typically bonded to a core with many open cavities or cells to maximize strength and minimize weight. This "honeycomb" structure renders the wing core particularly susceptible to corrosion. Furthermore, the core is uninspectable without damaging the skin. In such a wing, one or more anode wires may be laid along the length of the wing between the core and the skin.

The ends of each anode wire are connected across a device for measuring resistivity. While the area in which the anode wires are placed is dry, no corrosion occurs. So long as no moisture reaches the anode wires, the monitoring system provides an indication that no structural corrosion is occurring or foreseeable. The presence of moisture between an anode wire and the structure being monitored creates a current path. The anode wire will begin to corrode, but the structural members forming the cathode of the galvanic circuit remain uncorroded. At this point, the monitoring system may provide a warning or indication that a moisture intrusion has occurred.

The time remaining before the anode is completely consumed can be estimated from the rate at which the anode resistance increases as it corrodes. If the anode wire is completely consumed, the structure begins to corrode. An infinite resistance indicates that the anode has completely corroded. The monitoring system provides an indication that structural corrosion will occur after that time. If the moisture increases or decreases, the monitoring system updates the estimate based on the new rate of resistance increase. When the time remaining before the onset of structural corrosion reaches a predetermined time, the aircraft may be scheduled for maintenance. The maintenace may be scheduled to coincide with the onset of corrosion or to be performed at a later time, after a predetermined amount of structural corrosion has occurred.

Although a single anode wire is adequate to detect corrosion, multiple anode wires may be used to localize the area of corrosion. The resistivity of individual anode wires or groups of anode wires may be measured to provide a localized indication of corrosion.

The measuring device need not remain connected to the anode wire during flight. The anode wire or wires may extend through the wing core and be terminated in a suitable connector. The measuring device is then connected at scheduled maintenance intervals to determine whether a moisture intrusion has occurred. The connector may be disposed on the wing or on the inside or outside of the fuselage.

The foregoing, together with other features and advantages of my invention, will become more apparent when referring to the following specification, claims, and accompanying drawings.

BRIEF DESCRIPTION OF THE DRAWINGS

For a more complete understanding of my invention, I now refer to the following detailed description of the embodiments illustrated in the accompanying drawings, wherein.

DESCRIPTION OF THE PREFERRED EMBODIMENTS

Figure 1:
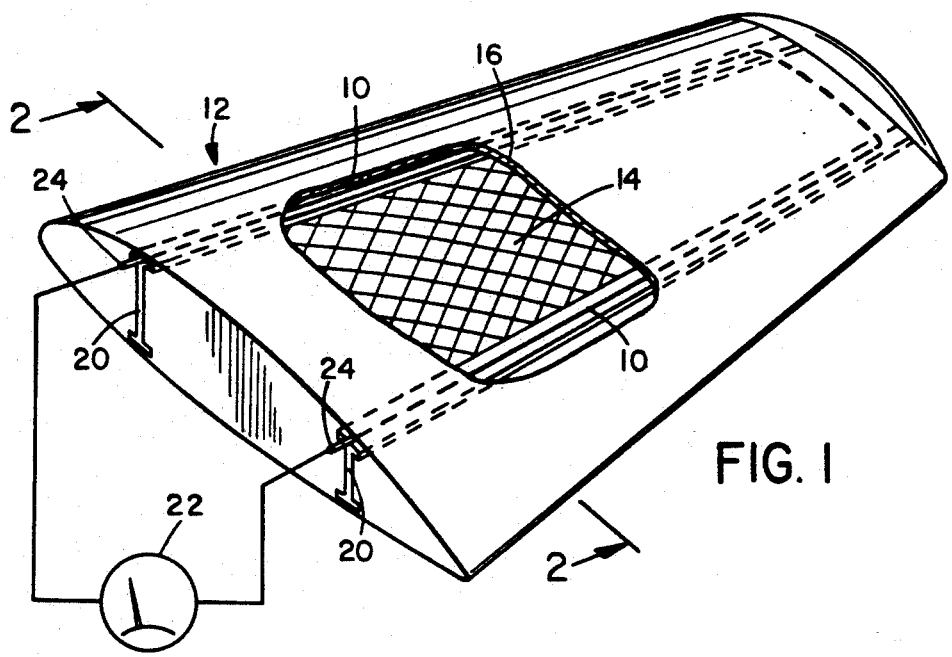
FIG. 1 illustrates a typical aircraft wing of bonded construction, partially cut away, incorporating the corrosion sensing monitor of the present invention.
Figure 2:
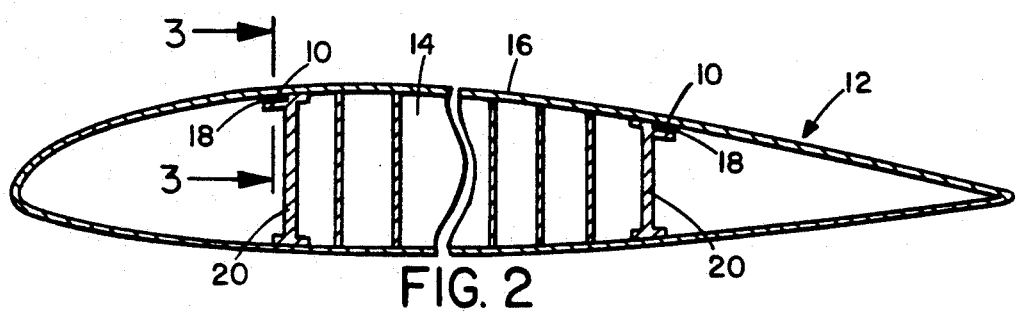
FIG. 2 is an enlarged sectional view taken on line 2—2 of FIG. 1.
Figure 3:
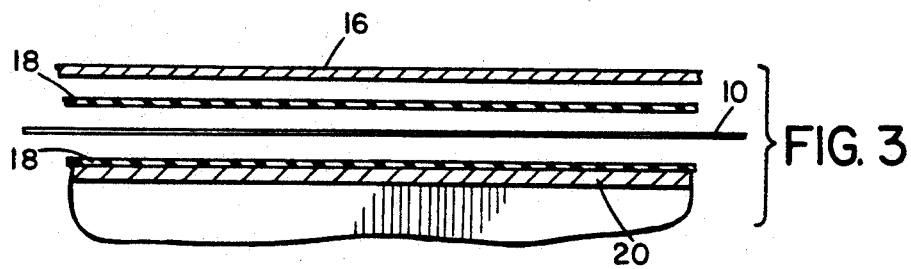
FIG. 3 is a further enlarged exploded view taken on line 3-3 of FIG. 2.

Although the present invention may be used to monitor galvanic corrosion of many types of structures, it is especially useful for monitoring corrosion in aircraft because of its minimal weight and ease with which it may be incorporated into existing aircraft designs. A wire is the preferred anode shape because it permits a large area to be covered with a minimal impact on weight. In FIGS. 1-3, an anode wire 10 is disposed inside an aircraft wing 12 having a sealed "honeycomb" core 14. Anode wire 10 is made of a suitable material that corrodes preferentially with respect to core 14. Anode wire 10 need not have a diameter greater than about 0.005 inches (0.013 cm), although a thicker anode wire will not degrade operation. Zinc is the preferred anode material for a wing having an aluminum honeycomb core.

Anode wire 10 is preferably disposed between core 14 and skin 16 of wing 12 and may be sandwiched between layers of insulating material 18 as shown in FIG. 3. The location of anode wire 10 within wing 12 is not critical, although it should be placed as near as practical to potential sources of moisture intrusions. The joints where the leading and trailing edges are attached to the main wing section are such sources. Furthermore, it may be convenient to secure anode wire 10 to the structural spars 20, which are often located near the leading and trailing edge joints. Anode wire 10 may be attached to spars 20 or other members using any suitable fastening means (not shown) such as a porous adhesive.

A measuring device 22 for measuring electrical resistance is connected across anode wire 10, which exits the wing at a point adjacent to the fuselage. Measuring device 22 may be located aboard the aircraft in any convenient area of the fuselage. Measuring device 22 continuously measures the resistance of anode wire 10 and continuously calculates the rate at which the resistance changes.

In an alternative embodiment, measuring device 22 may be periodically connected for diagnostic maintenance. In this embodiment, the aircraft wing need only contain the anode wire and a connector 24 for attaching the external measuring device. Connector 24 may be a single connector containing terminals corresponding to each end of anode wire 10 or two such connectors may be used. Connector 24 may extend through the fuselage wall, may be disposed on exterior of the wing, or may be disposed at any other convenient site. Connector 24 should be sealed from moisture penetration when not in use.

Figure 4:
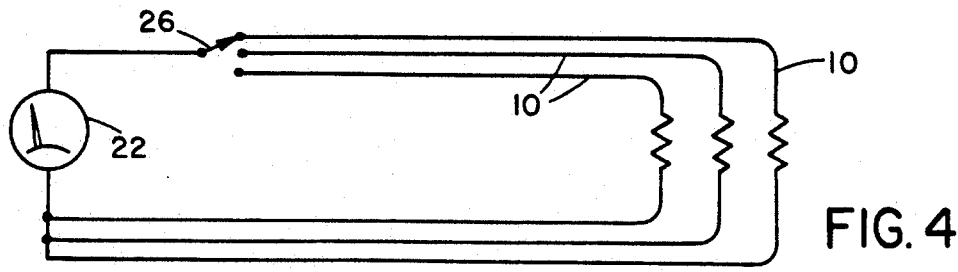
FIG. 4 is a wiring diagram of an embodiment of the present invention having multiple anode wires.

Referring to FIG. 4, any number of anode wires 10 may be distributed throughout the structure being monitored. A plurality of wires aids in localization of the moisture intrusion. In an embodiment having a plurality of anode wires 10, a switch or multiplexor 26 may be used to selectively route individual anode wires 10 to measuring device 22.

If a moisture intrusion occurs, anode wire 10 will begin to corrode before core 14, which will remain undamaged until all the anode material has been consumed in the electrochemical corrosion process. Core 14 will not begin to corrode until anode wire 10 has completely corroded through, i.e., after its resistance has become infinite.

Measuring device 22, in addition to calculating a rate of change of resistance, extrapolates the resistance using the present rate of change to the point in time where the resistance is infinite. Measuring device 22 may provide an indication of the time remaining until that point, which is indicative of the time remaining before the onset of corrosion in wing core 14. Practitioners in the art will understand that the resistance information may be processed using techniques known in the art to average or filter the resistance data or rate data. Measuring device 22 may incorporate a computer for processing resistance values sampled at suitable intervals. Alternatively, or in addition to predicting the time remaining before corrosion occurs, measuring device 22 may provide maintenance personnel with the date on which structural corrosion is predicted to occur.

Obviously, other embodiments and modifications of the present invention will occur readily to those of ordinary skill in the art in view of these teachings. Therefore, this invention is to be limited only by the following claims, which include all such other embodiments and modifications when viewed in conjunction with the above specification and accompanying drawings.

I claim:

1. A corrosion monitor for providing an indication of the time remaining before the onset of galvanic corrosion of a structure, comprising:
    at least one anode wire having two ends and a resistance, each said anode wire comprising a material corroding preferentially with respect to said structure and placed adjacent to said structure for creating a galvanic circuit between said anode wire and said structure in the presence of moisture; and
    measuring means connected to said ends of said anode wires for measuring said resistance, calculating a rate of change of said resistance, and extrapolating said rate of change to provide an indication of said time remaining before the onset of galvanic corrosion of said structure.

2. The corrosion monitor described in claim 1, wherein said structure comprises a volume insulated from moisture intrusion.

3. The corrosion monitor described in claim 2, wherein:
    said volume comprises an aircraft wing having a core and a skin;
    said anode wire being mounted between said core and said skin.

4. The corrosion monitor described in claim 1, wherein said anode wire is mounted to said structure with a porous adhesive.

5. The corrosion monitor described in claim 1, wherein said anode wire material is Zinc.

6. A corrosion monitor for providing an indication of the time remaining before the onset of galvanic corrosion of a structure, comprising:
    an enclosure sealed against moisture intrusion, said enclosure surrounding said structure;
    at least one anode wire disposed in said sealed enclosure, said anode wire having two ends and a resistance, each said anode wire comprising a material corroding preferentially with respect to said structure for creating a galvanic circuit between said anode wire and said structure in the presence of moisture; and
    measuring means connected to said ends of said anode wires for measuring said resistance.

7. The corrosion monitor described in claim 6, wherein:
    said enclosure comprises an aircraft wing having a core and a skin; and
    said anode wire being mounted between said core and said skin.

8. The corrosion monitor described in claim 1, wherein said anode wires are mounted to said structure with a porous adhesive.

9. The corrosion monitor described in claim 1, wherein said anode wire material is Zinc.

10. A method for determining the time remaining before the onset of galvanic corrosion of a structure, said structure having at least one anode wire having two ends and a resistance, each said anode wire comprising a material corroding preferentially with respect to said structure, comprising the steps of:
    connecting measuring means for measuring resistance across said ends of each said anode wire;
    calculating a rate of change of said resistance; and
    extrapolating said rate of change of said resistance to provide an indication of said time remaining before the onset of galvanic corrosion of said structure.

* * * * *